(12) United States Patent
Schamp (10) Patent No.: US 9,041,789 B2
(45) Date of Patent: May 26, 2015

(54) SYSTEM AND METHOD FOR DETERMINING DRIVER ALERTNESS (75) Inventor: Gregory G. Schamp, South Lyon, MI (US)

(73) Assignee: TK Holdings Inc., Auburn Hills, MI (US)

( * ) Notice: Subject to any disclaimer, the term of this patent is extended or adjusted under 35 U.S.C. 154(b) by 419 days.

(21) Appl. No.: 13/428,365

(22) Filed: Mar. 23, 2012

(65) Prior Publication Data

US 2012/0242819 A1 Sep. 27, 2012

Related U.S. Application Data (60) Provisional application No. 61/467,849, filed on Mar. 25, 2011.

(51) Int. Cl.
*H04N 9/47* (2006.01)
*G08B 21/06* (2006.01)
*A61B 5/18* (2006.01)
*B60K 28/06* (2006.01)
*G06K 9/00* (2006.01)

(52) U.S. Cl.
CPC . *G08B 21/06* (2013.01); *A61B 5/18* (2013.01); *B60K 28/066* (2013.01); *G06K 9/00228* (2013.01); *G06K 9/00845* (2013.01)

(58) Field of Classification Search
CPC .......... G08B 21/06; A61B 3/113; A61B 5/18; G06K 9/00604; G06K 9/00597; G06K 9/00228; G06K 9/00845; B60K 28/066
USPC ......................................................... 348/78
See application file for complete search history.

(56) References Cited

U.S. PATENT DOCUMENTS

| 5,034,679 | A | | 7/1991 | Henderson et al. | |
|---|---|---|---|---|---|
| 5,351,044 | A | * | 9/1994 | Mathur et al. | 340/901 |
| 5,689,241 | A | | 11/1997 | Clarke et al. | |
| 6,092,014 | A | | 7/2000 | Okada | |
| 6,172,600 | B1 | * | 1/2001 | Kakinami et al. | 340/435 |
| 6,313,749 | B1 | * | 11/2001 | Horne et al. | 340/575 |
| 6,756,903 | B2 | * | 6/2004 | Omry et al. | 340/576 |
| 6,927,694 | B1 | * | 8/2005 | Smith et al. | 340/576 |

(Continued)

FOREIGN PATENT DOCUMENTS

| JP | 08-115500 A | 5/1996 |
|---|---|---|
| JP | 08-202991 A | 8/1996 |

(Continued)

OTHER PUBLICATIONS

International Search Report dated Oct. 18, 2012 issued in connection with International Application No. PCT/US2012/030162.

(Continued)

*Primary Examiner* — Shan Elahi
(74) *Attorney, Agent, or Firm* — Foley & Lardner LLP (57) ABSTRACT

A driver alertness detection system includes an imaging unit configured to image an area in a vehicle compartment where a driver's head is located; an image processing unit configured to receive the image from the imaging unit, and to determine positions of the driver's head and eyes; and a warning unit configured to determine, based on the determined position of the driver's head and eyes as output by the image processing unit, whether the driver is in an alert state or a non-alert state, and to output a warning to the driver when the driver is determined to be in the non-alert state.

25 Claims, 9 Drawing Sheets

(56) References Cited

U.S. PATENT DOCUMENTS

| | | | |
|---|---|---|---|
| 7,639,148 B2 | 12/2009 | Victor | |
| 7,647,180 B2 | 1/2010 | Breed | |
| 7,751,973 B2 | 7/2010 | Ibrahim | |
| 7,755,682 B2 | 7/2010 | Lin | |
| 7,788,008 B2 | 8/2010 | Breed | |
| 7,835,834 B2 | 11/2010 | Smith et al. | |
| 7,840,355 B2 | 11/2010 | Breed et al. | |
| 7,876,957 B2 | 1/2011 | Ovsiannikov et al. | |
| 7,899,616 B2 | 3/2011 | Breed | |
| 7,970,172 B1 | 6/2011 | Hendrickson | |
| 8,000,897 B2 | 8/2011 | Breed et al. | |
| 8,004,588 B2 | 8/2011 | Lukac | |
| 8,005,297 B2 | 8/2011 | Hung et al. | |
| 8,035,704 B2 | 10/2011 | Hu et al. | |
| 8,036,788 B2 | 10/2011 | Breed | |
| 8,044,789 B2* | 10/2011 | Daura Luna et al. | 340/463 |
| 8,077,921 B2* | 12/2011 | Kawasaki | 382/104 |
| 8,248,220 B2* | 8/2012 | Nagamine et al. | 340/435 |
| 8,314,707 B2* | 11/2012 | Kobetski et al. | 340/575 |
| 8,331,621 B1* | 12/2012 | Allen et al. | 382/104 |
| 8,385,600 B2 | 2/2013 | Nara et al. | |
| 2002/0118212 A1* | 8/2002 | Lake et al. | 345/606 |
| 2004/0022416 A1* | 2/2004 | Lemelson et al. | 382/104 |
| 2005/0083211 A1 | 4/2005 | Shafir et al. | |
| 2005/0226472 A1 | 10/2005 | Komura | |
| 2005/0232461 A1* | 10/2005 | Hammoud | 382/103 |
| 2006/0048800 A1* | 3/2006 | Rast et al. | 134/56 R |
| 2006/0215076 A1 | 9/2006 | Karim | |
| 2007/0154068 A1* | 7/2007 | Stein et al. | 382/106 |
| 2008/0069400 A1* | 3/2008 | Zhu et al. | 382/103 |
| 2009/0109648 A1 | 4/2009 | Hay | |
| 2010/0253495 A1* | 10/2010 | Asano et al. | 340/439 |
| 2010/0274641 A1* | 10/2010 | Allen et al. | 705/13 |
| 2011/0046843 A1 | 2/2011 | Caveney | |
| 2011/0054716 A1 | 3/2011 | Stahlin et al. | |
| 2011/0068934 A1* | 3/2011 | Weng et al. | 340/575 |
| 2011/0098922 A1 | 4/2011 | Ibrahim | |
| 2012/0288154 A1* | 11/2012 | Shima et al. | 382/103 |
| 2013/0021462 A1* | 1/2013 | Kadoya et al. | 348/78 |

FOREIGN PATENT DOCUMENTS

| | | |
|---|---|---|
| JP | 2002-260190 A | 9/2002 |
| JP | 2006-111184 A | 4/2006 |
| JP | 2007-106170 A | 4/2007 |
| WO | WO-2009/060172 | 5/2009 |

OTHER PUBLICATIONS

Written Opinion of the International Searching Authority dated Oct. 18, 2012 issued in connection with International Application No. PCT/US2012/030162.

Office Action dated Sep. 25, 2013 issued in connection with U.S. Appl. No. 13/427,808.

Extended European Search Report dated Oct. 10, 2014 issued in European Application No. 12765209.

* cited by examiner

SYSTEM AND METHOD FOR DETERMINING DRIVER ALERTNESS

This application claims priority from Provisional Application 61/467,849, filed Mar. 25, 2011, incorporated herein by reference in its entirety. The present disclosure relates generally to the field of driver monitoring systems. More specifically, the present disclosure relates to a system and method for determining the alertness of a driver using image processing to assess the head position and eye vector of the driver.

BACKGROUND

Driver monitoring systems are becoming more and more popular for inclusion in vehicles, so as to warn a driver when the driver is detected to be in a non-alert state.

SUMMARY OF THE INVENTION

According to one exemplary embodiment, a driver alertness detection system includes an imaging unit configured to image an area in a vehicle compartment where a driver's head is located; an image processing unit configured to receive the image from the imaging unit, and to determine positions of the driver's head and eyes; and a warning unit configured to determine, based on the determined position of the driver's head and eyes as output by the image processing unit, whether the driver is in an alert state or a non-alert state, and to output a warning to the driver when the driver is determined to be in the non-alert state.

According to another exemplary embodiment, a method of detecting driver alertness includes imaging an area in a vehicle compartment where a driver's head is located, to obtain imaging data; determining positions of the driver's head and eyes based on the imaging data; based on the determined position of the driver's head and eyes, determining whether the driver is in an alert state or a non-alert state; and outputting a warning to the driver when the driver is determined to be in the non-alert state.

According to yet another exemplary embodiment, a non-transitory computer readable medium storing computer program code that, when executed by a computer, causes the computer to perform the functions of imaging an area in a vehicle compartment where a driver's head is located, to obtain imaging data; determining positions of the driver's head and eyes based on the imaging data; determining, based on the determined position of the driver's head and eyes, whether the driver is in an alert state or a non-alert state; and outputting a warning to the driver when the driver is determined to be in the non-alert state.

BRIEF DESCRIPTION OF THE DRAWINGS

These and other features, aspects, and advantages of the present invention become apparent from the following description and the accompanying exemplary embodiments shown in the drawings, which are briefly described below.

DETAILED DESCRIPTION

The incidence of single-vehicle and multi-vehicle accidents continues to increase due to driver distraction from increasingly sophisticated communication and entertainment devices. Drivers are increasingly distracted by cell phones which can function as a variety of devices such as instant messengers, cameras, GPS navigation systems, internet web browsers, movie players, and spreadsheet analysis tools. The allure of these applications tempts both novice and experienced drivers from actively comprehending their lane position, distance to other vehicles, traffic signals, and roadway boundaries.

Figure 1:
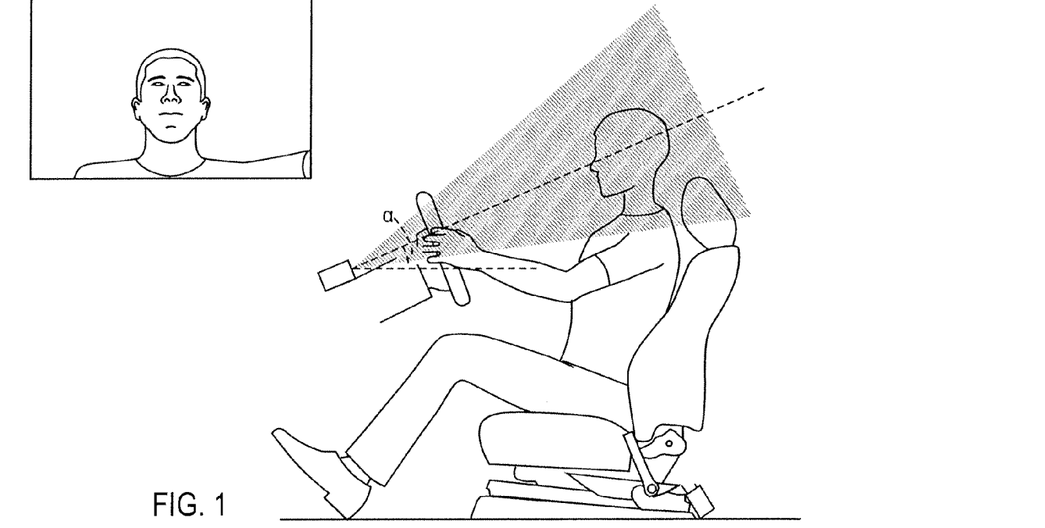
FIG. 1 is a schematic view of camera placement and coverage for a driver alertness system according to an exemplary embodiment.
Figure 2:
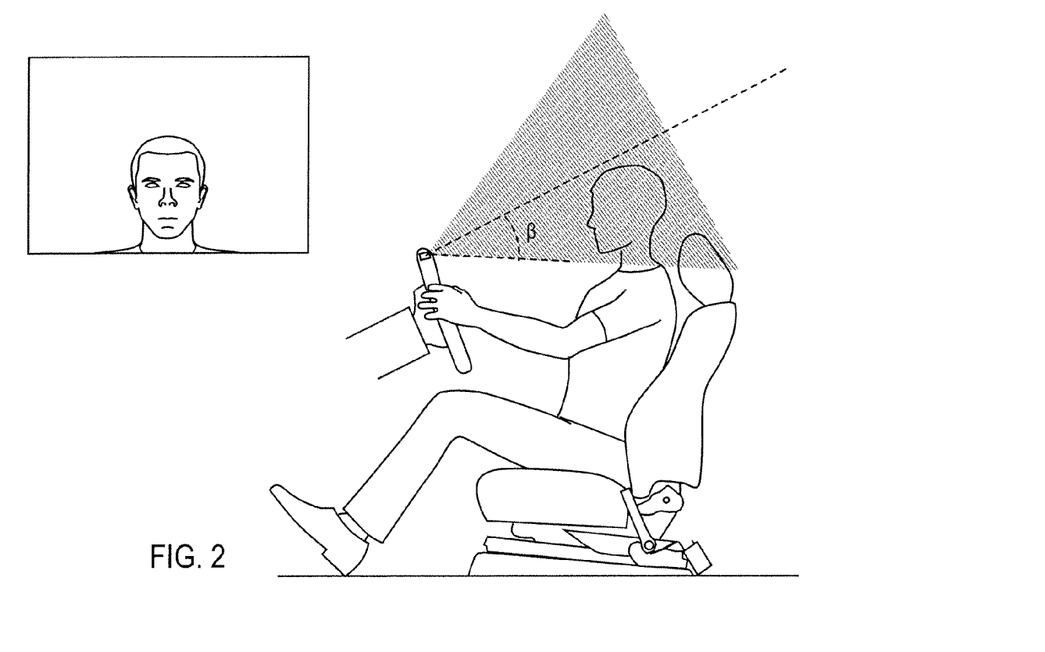
FIG. 2 is a schematic view of camera placement and coverage for a driver alertness system according to an exemplary embodiment.

According to an exemplary embodiment, a driver alertness system is provided to monitor the alertness of a driver and issue a warning if it is determined that the driver is distracted for a sufficient period. Referring to FIGS. 1 and 2, the driver alertness system computes the position of the driver's head and eye vector using a monocular camera mounted in the instrument panel or in the steering wheel. The instrument panel mounting provides broader coverage of the passenger compartment making it unlikely that the driver would ever leave the field of view. The steering wheel mounting emphasizes the driver's facial features, but can be easily covered with a hand. The rotation of the steering wheel is considered to be an intentional maneuver, indicating that the driver is at high alertness. Therefore, the driver alertness algorithm is disabled until returning to the central position (e.g., +/−15 degrees from vertical).

The instantaneous positional reports of the driver's head and eye vector are aggregated over short time durations and used to determine where the driver's attention is focused using a driver alertness algorithm. If the driver's attention is not adequately focused upon a calibrated forward-looking region, a warning signal will be given to the driver. The warning signal is a signal that is able to be conveyed to the driver regardless of where the driver's attention is. A wide variety of audio, visual, or tactile warnings signals may be issued, including an in-dash buzzer or vibration sent through the driver's seat with a motorized cam operating on the seat pan.

Figure 3:
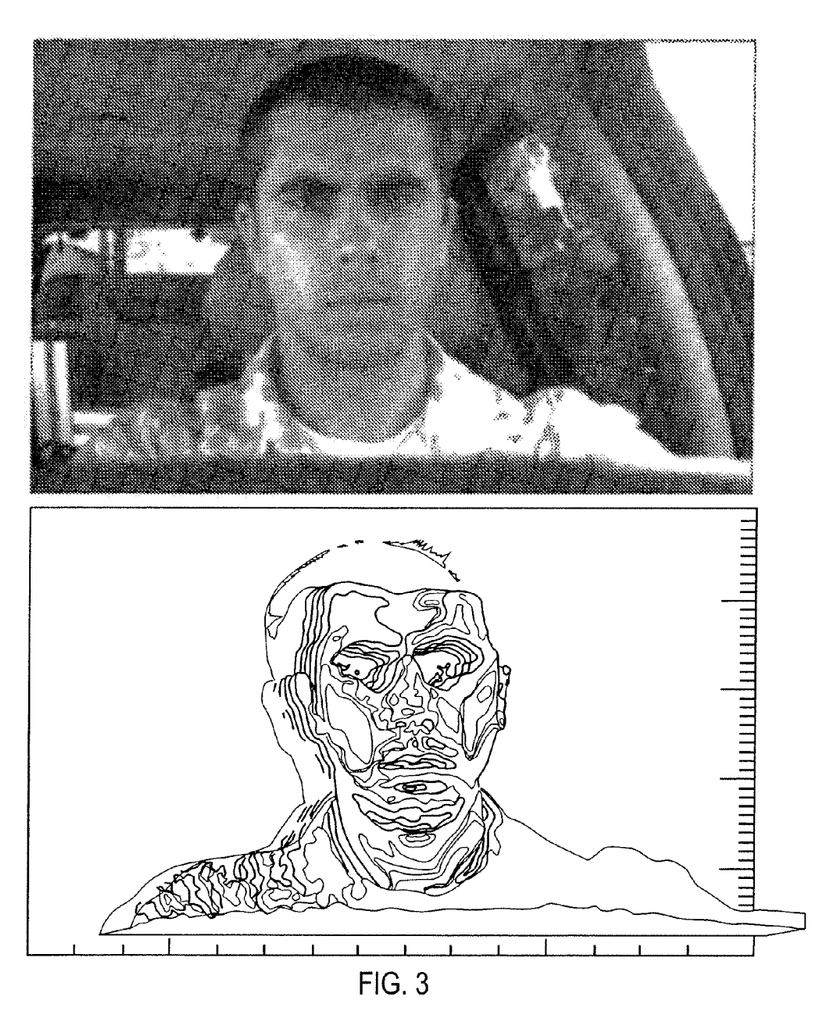
FIG. 3 is a flat two-dimensional intensity image captured by a camera for a driver alertness system and a corresponding 2.5-dimensional pseudo-depth image according to an exemplary embodiment.

According to an exemplary embodiment, the driver alertness algorithm includes two independent detection modules operating on image data, such as a 752-column×480-row 10-bit intensity image. The first detection module discriminates background structures from the driver's silhouette and computing head rotation (turning left or right) and tilt/roll (touching ear to shoulder). The second detection module identifies head pitch, control points from discernable facial structures (eyes, nostrils, and lips), and a matrix of inter-point metrics. Both modules derive a pseudo-depth scale from image intensity gradients using a Gouraud shading model or other suitable shading model. Referring to FIG. 3, this technique transforms the flat two-dimensional intensity image into a 2.5-dimensional pseudo-depth image. The transformation to pseudo-depth image facilitates isolating facial features and dropping unwanted background clutter. The 2.5-dimensional pseudo-depth image transformation is a technique used to restore depth-of-field relative to the camera's focal plane array.

Figure 4:
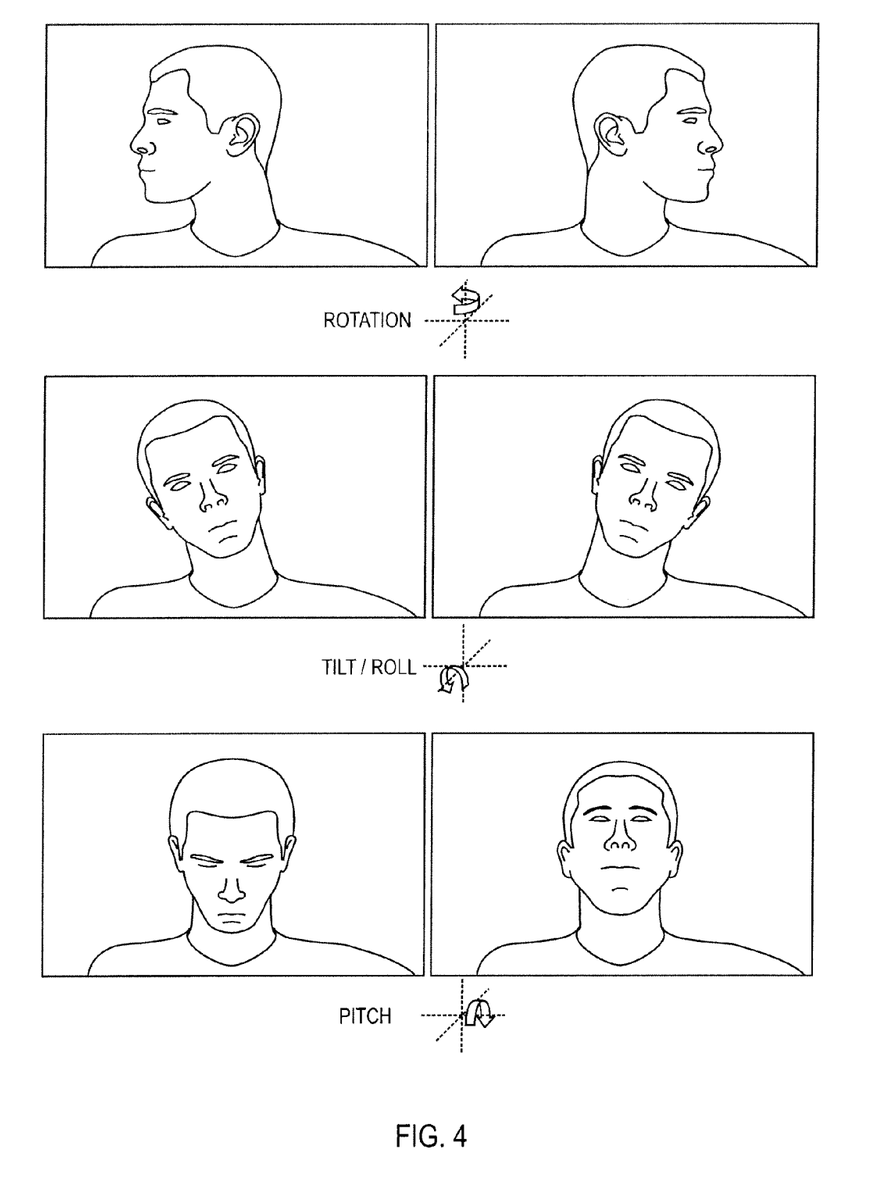
FIG. 4 is a series of images of a driver showing various head movements according to an exemplary embodiment.

Referring to FIG. 4, with the torso remaining essentially stationary, motions of the head can be categorized by the axis of rotation. Rotation about a vertical axis causes the head to turn to the left and right. Rotation about a horizontal axis oriented front to back causes the head to tilt or roll to the left or right. Rotation about a horizontal axis oriented left to right causes the head to pitch forward and back.

Figure 5:
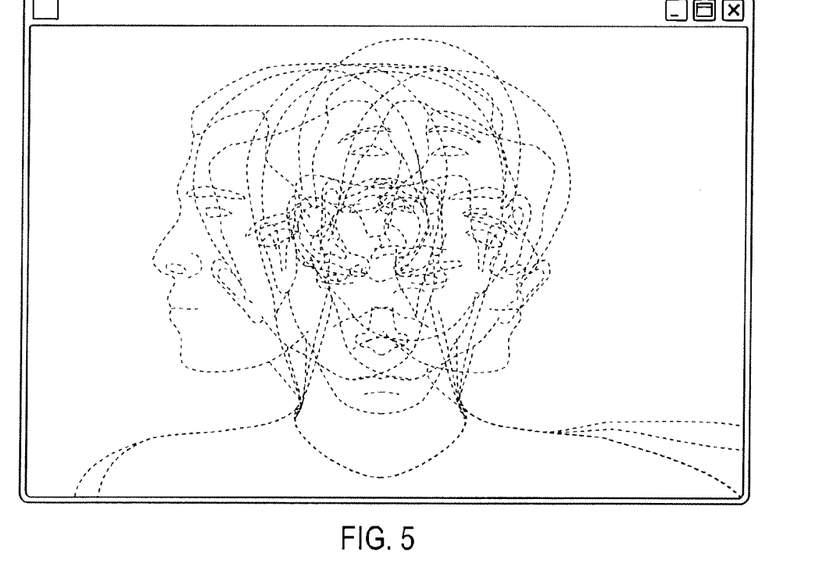
FIG. 5 is a composite of images of the head movements of multiple drivers according to an exemplary embodiment.
Figure 6:
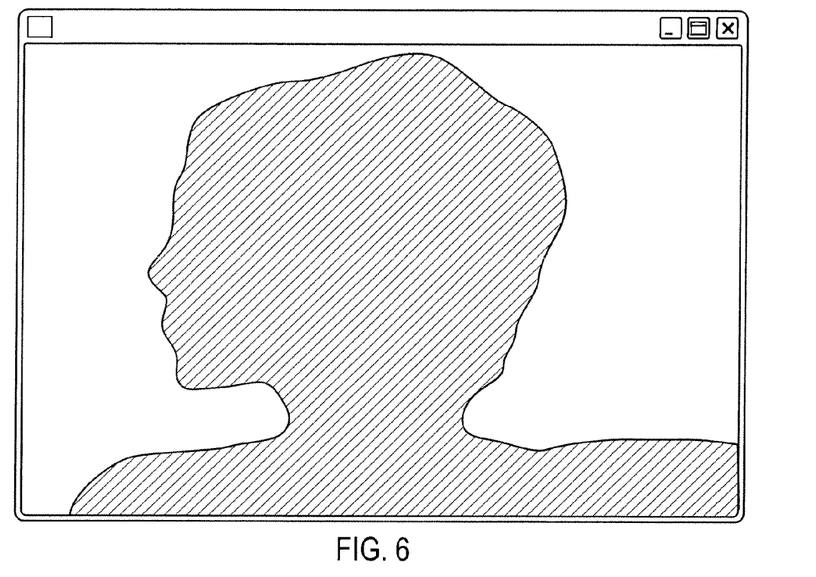
FIG. 6 is a high-occupancy region-of-interest determined from the composite image of FIG. 5 according to an exemplary embodiment.

Referring to FIGS. 5 and 6, a high-occupancy region-of-interest can be constructed by forming a composite of the head movements (e.g., the movements shown in FIG. 4) of multiple drivers. According to one exemplary embodiment, a high-occupancy region-of-interest is constructed from a study of eight different drivers during a combined 30 minutes of driving time. The high-occupancy region-of-interest provides a 2-dimensional likelihood of the driver's head position and shows low-probability regions that are considered clutter. The contrast within the high-probability regions can be enhanced with a sigmoidal filter or other suitable filter, allowing for optimized intensity gradients, and robust detection results under highly dynamic lighting conditions.

Figure 7A:
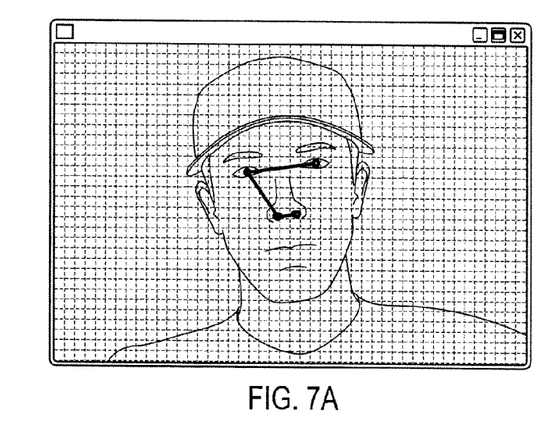
FIG. 7A is an image captured for a driver alertness system showing the camera coordinate system and facial feature detection points according to an exemplary embodiment.
Figure 7B:
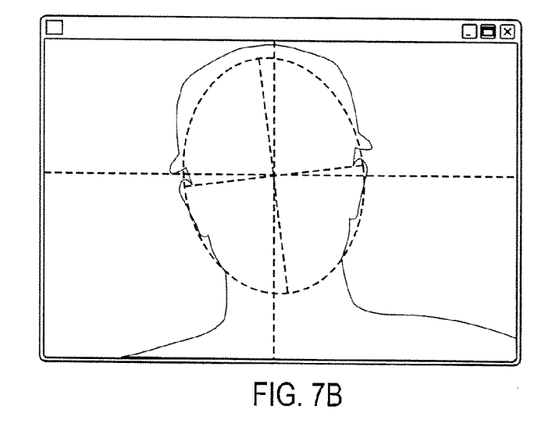
FIG. 7B is a detected silhouette of the head of the driver in the image of FIG. 7A showing the principle axis rotation angle.
Figure 7C:
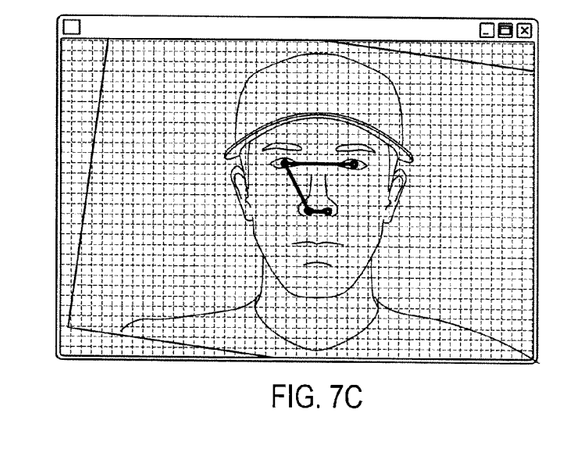
FIG. 7C is the image of FIG. 7A after being rotated to align the principle axis in FIG. 7B with the camera coordinate system.
Figure 7D:
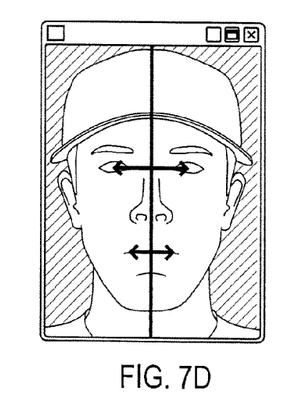
FIG. 7D is a detected facial region of the captured image of FIG. 7A after being aligned with the camera coordinate grid.

Referring to FIGS. 7A-7D, a principal axis transform is used to align the driver's silhouette and facial control points to the camera's coordinate grid. The classification of the driver's attention state is derived from the detected silhouette, facial control points, and inter-point metrics (geometric relationships between the detected control points) that are aligned to the camera's coordinate grid. An image of the driver's face is captured by a camera (see FIGS. 7A and 7C). The driver's silhouette is detected and the tilt relative to the coordinate grid is determined (see FIG. 7B). The driver attention algorithm then rotates the detected facial region of the captured image to be aligned with the camera's coordinate grid (see. FIG. 7D) with symmetry of eyes and lips.

Alignment to the coordinate grid, using a principal axis transform, normalizes facial geometry and simplifies the search for related facial features. Control points on the driver's eyes, nostrils, and lips are rotated to be collinear, reducing the likelihood the system will confuse an eye with a nostril. Without the principal axis transformation, the matrix of inter-point metrics could contain corrupted measurements from mismatched facial control points.

Figure 8A:
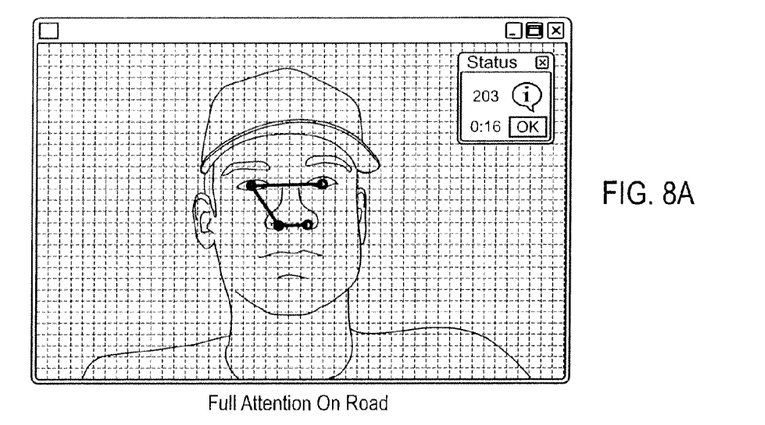
FIGS. 8A-8C are a series of images showing the geometric relationships between facial structures under a variety of head and eye movements and calibration steps for registering driver attention while looking at predetermined points within a vehicle according to an exemplary embodiment.
Figure 8B:
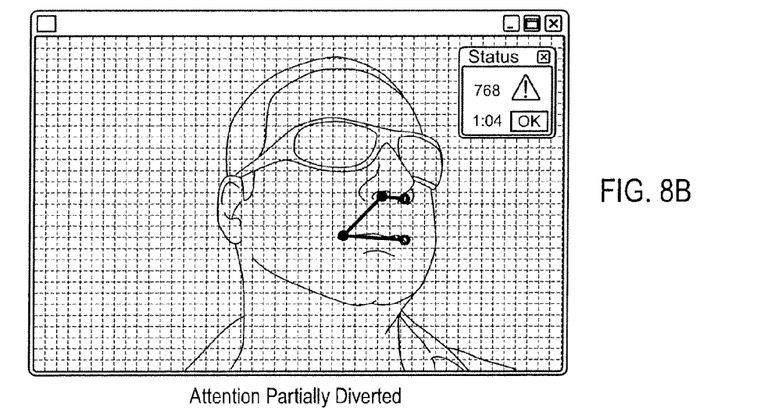
Figure 8C:
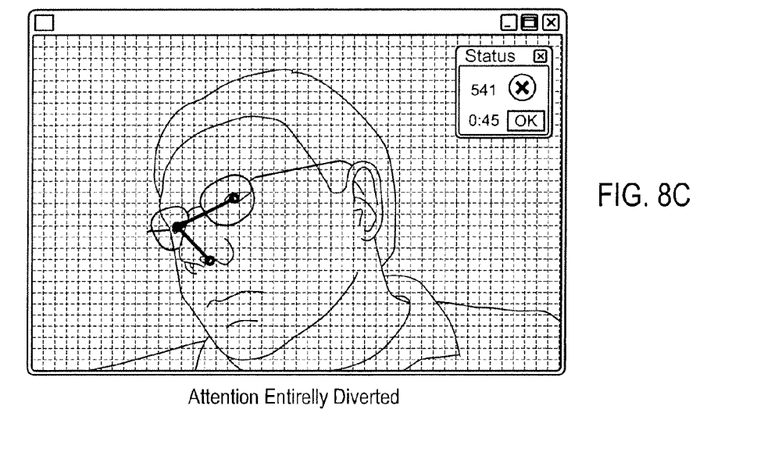

Referring to FIGS. 8A-8C, examples are shown of geometric relationships between facial structures and calibration steps for registering driver attention while looking at predetermined points within a vehicle. A classification training process is used to register a driver's head position and eye vector at several pre-determined points (e.g., A-pillars, instrument panel, outside mirrors, rear-view mirror, windshield, passenger floor, center console, radial, and climate controls) within a specific vehicle. The matrix of inter-point metrics is saved and used for a look-up-table classification of the driver's attention state. FIG. 8A is an image showing a driver in a full-alert state, FIG. 8B is an image showing a driver in an attention partially diverted state, and FIG. 8C is an image showing a driver in an attention entirely diverted state. Based on the detected state, an appropriate warning is provided to the driver. For example, if the driver is detected to be in an attention partially diverted state, a mild warning is provided to the driver, such as by way of an audible alarm of a first sound level, and when the driver is detected to be in an attention fully diverted state, a loud warning is provided to the driver, such as by way of an audible alarm of a second sound level greater in intensity than the first sound level (e.g., 20 dB greater in sound level), whereby a buzzer or other type of tactile warning can also be provided to the driver in both cases (with the vibration being greater for the attention fully diverted state).

Figure 9:
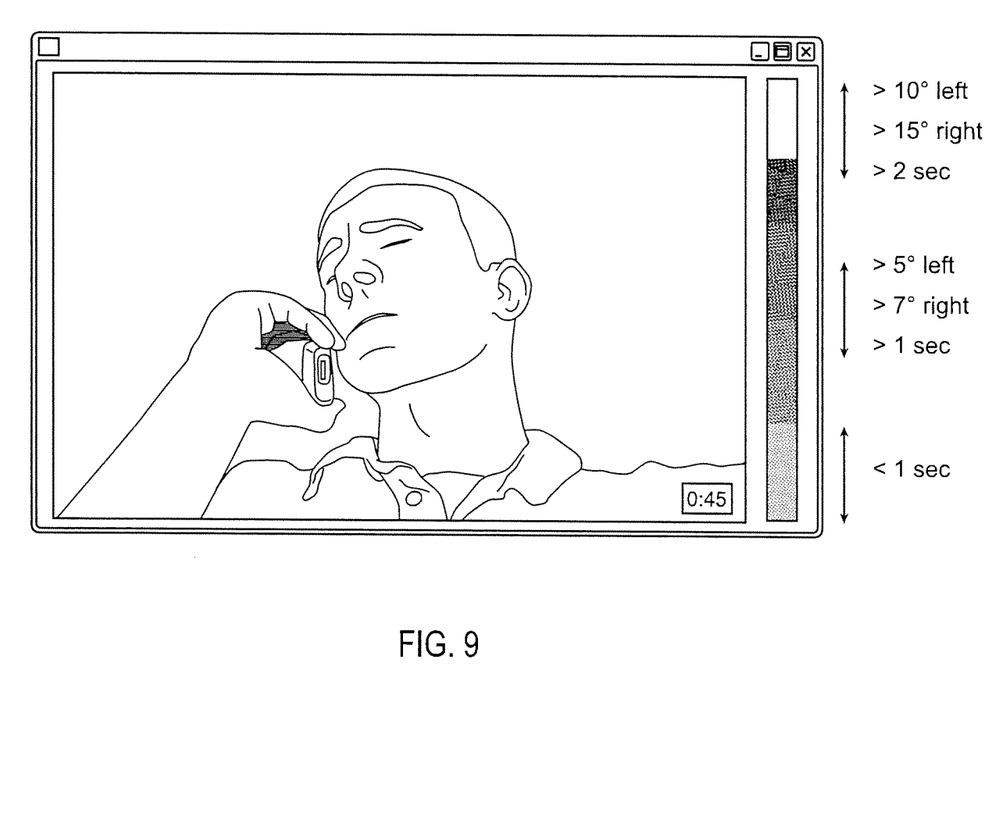
FIG. 9 is an image of a graphical user interface for a driver alertness system according to an exemplary embodiment.

Referring to FIG. 9, an exemplary interface and warning scale is shown. The instantaneous classification of driver attention state is accumulated into a moving average filter of 1-second durations. The angular deviation from a forward looking position and time duration of the angular deviation determine whether a warning will be issued to the driver. The sensitivity of this warning is tuned to avoid excessive false positives which may desensitize and irritate the driver and reduce the effectiveness of the driver alertness system.

Figure 10:
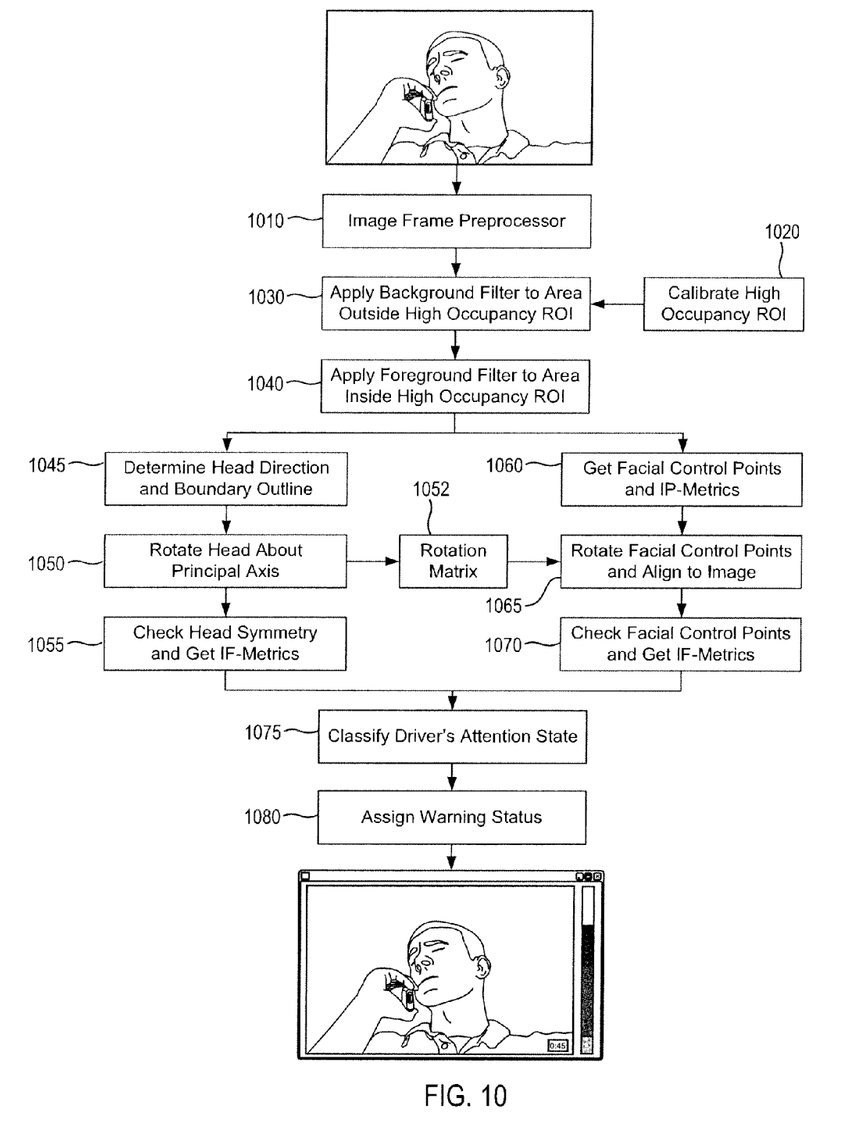
FIG. 10 is a flowchart for an algorithm for a driver alertness system according to an exemplary embodiment.

Referring to FIG. 10, a flow chart for the driver alertness algorithm is shown according to an exemplary embodiment. An image is captured by an image frame preprocessor in step 1010. The image is then processed using a previously calibrated high occupancy region of interest in step 1020. The portion of the image outside of the high occupancy region of interest is processed with a background filter in step 1030. The portion of the image inside the high occupancy region of interest is processed with a foreground filter in step 1040. After being filtered, the image is then processed to detect the head position and position of facial control points.

The algorithm detects the head and outlines the boundary of the head in step 1045. The head is then rotated about the principle axis to align it with the camera's coordinate system in step 1050, whereby a rotation matrix 1052 is created. The head symmetry is then analyzed to determine the orientation of the driver's head relative to a forward-facing orientation in step 1055.

The algorithm also detects facial control points from the captured image in step 1060. The facial control points are then rotated to match the rotation of the head about the principal axis in step 1065 (using the rotation matrix 1052). The facial control points are then analyzed using inter-point metrics to determine the orientation of the driver's face relative to a forward-facing orientation in step 1070. Inter-point metrics, or the relationships between the control points, may comprise a set of vectors connecting control points (e.g. vectors between any combination of pupils, nostrils, corners of the mouth, or other suitable control points).

In steps 1055 and 1070, inter-frame metrics may be used to determine changes in the position of the head over time (i.e. between image frames). As the head of the driver moves, the control points change positions. Correspondingly, the vectors between the control points shift (see, e.g., FIGS. 8A-8C). To track movements between captured image frames, the angles between the vectors may be measured. For example, changes in interior angles of the vectors between control points can be analyzed to track the changing position of the head.

Using the position of the head and facial control points, the algorithm classifies the attention state of the driver in step 1075. A warning status is then assigned based on the duration and magnitude of the driver's deviation from a forward-facing orientation in step 1080. The warning status may be used to activate a visual, audio, or tactile warning signal to the driver. The warning status and captured image may also be output to a graphical user interface.

The driver alertness algorithm determines a driver's attention state based on driver characteristics (head position and eye vector) and not what the vehicle is doing relative to roadway lane markers (lane departure warning systems). The driver alertness algorithm has the advantage of warning an inattentive driver before his vehicle deviates from roadway boundaries. The driver alertness algorithm uses interior vision sensing which is more robust than exterior sensing during nighttime and high dynamic range conditions (going through a tunnel with on-coming vehicle headlights).

Figure 11:
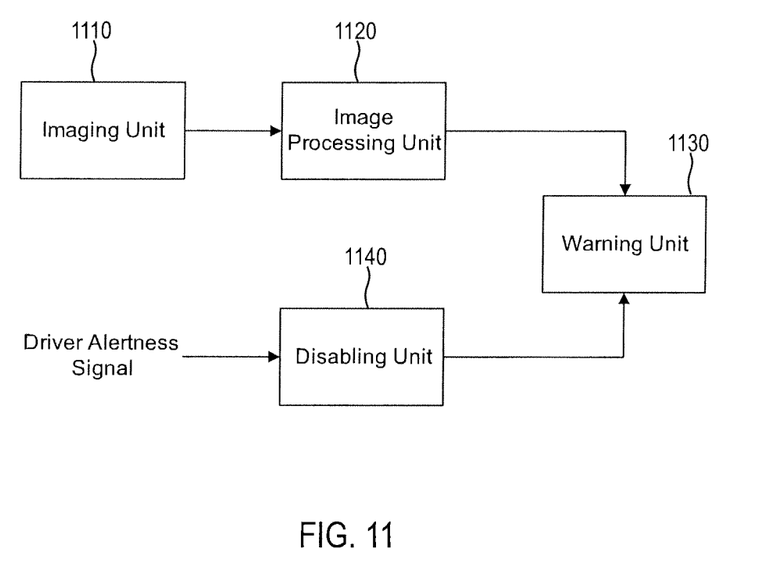
FIG. 11 is a driver alertness system according to an exemplary embodiment.

Referring to FIG. 11, a flow chart for a driver alertness system is shown according to an exemplary embodiment. An imaging unit 1110 images an area in a vehicle compartment where a driver's head is located. The imaging unit 1110 may comprise, for example, a monocular camera mounted in an instrument panel of the vehicle or in a steering wheel. An image processing unit 1120 receives the image from the imaging unit 1110 and determines positions of the driver's head and eyes. The image processing unit 1120 may comprise two detection modules, as described above. A warning unit 1130 determines, based on the determined position of the driver's head and eyes as output by the image processing unit 1120, whether the driver is in an alert state or a non-alert state. The warning unit 1130 outputs a warning to the driver when the driver is determined to be in the non-alert state. A disabling unit 1140 is also provided, which may temporarily disable the driver alertness detection system when a driver alertness signal is received. The driver alertness signal is triggered by the rotational position of the steering wheel. If the steering wheel has been rotated at least a predetermined amount from a center position, a driver alertness signal will be sent to the disabling unit 1140. The disabling unit 1140 will then prevent the warning unit 1130 from outputting a warning to the driver (because rotation of the steering wheel is considered to be an intentional maneuver indicating high alertness). On the other hand, when the steering wheel is returned to a substantially central position, the driver alertness signal will stop. The warning unit 1130 will then issue a warning if it has determined, based on the position of the driver's head and eyes as output by the image processing unit 1120, that the driver is in a non-alert state. The disabling unit 1140 may interfere with the outputs of any of the other units as shown in FIG. 11 at any suitable time.

The present disclosure has been described with reference to example embodiments, however persons skilled in the art will recognize that changes may be made in form and detail without departing from the spirit and scope of the disclosed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the exemplary embodiments is manifestly intended to be as broad as possible. For example, unless specifically otherwise noted, the exemplary embodiments reciting a single particular element also encompass a plurality of such particular elements.

Exemplary embodiments may include program products comprising computer or machine-readable media for carrying or having machine-executable instructions or data structures stored thereon. For example, the driver monitoring system may be computer driven. Exemplary embodiments illustrated in the methods of the figures may be controlled by program products comprising computer or machine-readable media for carrying or having machine-executable instructions or data structures stored thereon. Such computer or machine-readable media can be any available media which can be accessed by a general purpose or special purpose computer or other machine with a processor. By way of example, such computer or machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of computer or machine-readable media. Computer or machine-executable instructions comprise, for example, instructions and data which cause a general purpose computer, special purpose computer, or special purpose processing machines to perform a certain function or group of functions. Software implementations of the present invention could be accomplished with standard programming techniques with rule based logic and other logic to accomplish the various connection steps, processing steps, comparison steps and decision steps.

It is also important to note that the construction and arrangement of the elements of the system as shown in the preferred and other exemplary embodiments is illustrative only. Although only a certain number of embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the assemblies may be reversed or otherwise varied, the length or width of the structures and/or members or connectors or other elements of the system may be varied, the nature or number of adjustment or attachment positions provided between the elements may be varied. It should be noted that the elements and/or assemblies of the system may be constructed from any of a wide variety of materials that provide sufficient strength or durability. Accordingly, all such modifications are intended to be included within the scope of the present disclosure. The order or sequence of any process or method steps may be varied or re-sequenced according to alternative embodiments. Other substitutions, modifications, changes and omissions may be made in the design, operating conditions and arrangement of the preferred and other exemplary embodiments without departing from the spirit of the present subject matter.

What is claimed is:

1. A driver alertness detection system, comprising:
   an imaging unit configured to image an area in a vehicle compartment of a vehicle where a driver's head is located;
   an image processing unit configured to receive the image from the imaging unit, and to determine positions of the driver's head and eyes; and
   a warning unit configured to determine, based on the determined position of the driver's head and eyes as output by the image processing unit, whether the driver is in an alert state or a non-alert state, and to output a warning to the driver when the driver is determined to be in the non-alert state,
   wherein the image processing unit determines that the driver is in the non-alert state when the determined position of the driver's head is determined not to be within a predetermined driver head area region within the vehicle compartment or when the driver's eyes are determined to be angled to an extent so as to not be viewing an area in front of the vehicle.

2. The driver alertness detection system according to claim 1, further comprising:
   a disabling unit configured to temporarily disable the driver alertness detection system when a driver alertness signal is received.

3. The driver alertness detection system according to claim 2, wherein the driver alertness signal is output upon rotation of a steering wheel of the vehicle by at least a predetermined amount.

4. The driver alertness detection system according to claim 3, wherein the predetermined rotation amount corresponds to +/−15 degrees from a center position of the steering wheel.

5. The driver alertness detection system according to claim 3, wherein, when the driver alertness signal is being output, the driver alertness signal is stopped from being output when the steering wheel of the vehicle is returned back to a substantially central position.

6. The driver alertness detection system according to claim 1, wherein the imaging unit comprises a monocular camera mounted in at least one of an instrument panel of the vehicle and a steering wheel of the vehicle.

7. The driver alertness detection system according to claim 1, wherein the warning unit determines that the driver is in the non-alert state when the determined position of the driver's head as output by the image processing unit is not within a predetermined head location region for at least a first predetermined amount of time or when the determined positions of the driver's eyes are not within a predetermined eye location region within the vehicle compartment for at least a second predetermined amount of time.

8. The driver alertness detection system according to claim 1, wherein the alert output by the warning unit corresponds to one of an in-dash buzzer or a vibration sent through a seat of the driver.

9. The driver alertness detection system according to claim 1, wherein the image processing unit comprises:
   a first detection module that discriminates background structures from a silhouette of the driver and that computes rotation of the driver's head and tilt/roll of the driver's head; and
   a second detection module that discriminates pitch of the driver's head, computes control points from discernable facial structures of the driver's head, and computes a matrix of inter-point metrics with respect to the driver's head.

10. The driver alertness detection system according to claim 9, wherein the discernable facial structures comprise at least one of eyes, nostrils, and lips.

11. The driver alertness detection system according to claim 9, wherein the first and second detection modules utilize a Gouraud shading model to discriminate movement and position of the driver's head.

12. A method of detecting driver alertness, comprising:
   imaging an area in a vehicle compartment of a vehicle where a driver's head is located, to obtain imaging data;
   determining positions of the driver's head and eyes based on the imaging data;
   based on the determined position of the driver's head and eyes, determining whether the driver is in an alert state or a non-alert state; and
   outputting a warning to the driver when the driver is determined to be in the non-alert state,
   wherein the driver is determined to be in the non-alert state when the determined position of the driver's head is determined not to be within a predetermined driver head area region within the vehicle compartment or when the driver's eyes are determined to be angled to an extent so as to not be viewing an area in front of the vehicle.

13. The method according to claim 12, further comprising:
   temporarily disabling outputting of a warning when a driver alertness signal is received.

14. The method according to claim 13, further comprising:
   detecting rotation of a steering wheel of the vehicle,
   wherein the driver alertness signal is output upon rotation of the steering wheel of the vehicle by at least a predetermined amount.

15. The method according to claim 14, wherein the predetermined rotation amount corresponds to +/−15 degrees from a center position of the steering wheel.

16. The method according to claim 14, wherein, when the driver alertness signal is being output, the driver alertness signal is stopped from being output when the steering wheel of the vehicle is returned back to a substantially central position.

17. The method according to claim 12, wherein the imaging data is obtained by a monocular camera mounted in at least one of an instrument panel of the vehicle and a steering wheel of the vehicle.

18. The method according to claim 12, wherein the driver is determined to be in the non-alert state when the determined position of the driver's head as output by the image processing unit is not within a predetermined head location region for at least a first predetermined amount of time or when the determined positions of the driver's eyes are not within a predetermined eye location region within the vehicle compartment for at least a second predetermined amount of time.

19. The method according to claim 12, wherein the alert corresponds to one of an in-dash buzzer or a vibration sent through a seat of the driver.

20. The method according to claim 12, wherein determining positions of the driver's head comprises:
   discriminating background structures from a silhouette of the driver, and computing rotation of the driver's head and tilt/roll of the driver's head; and
   discriminating pitch of the driver's head, computing control points from discernable facial structures of the driver's head, and computing a matrix of inter-point metrics with respect to the driver's head.

21. The method according to claim 20, wherein the discernable facial structures comprise at least one of eyes, nostrils, and lips.

22. A non-transitory computer readable medium storing computer program code that, when executed by a computer, causes the computer to perform the functions of:
- imaging an area in a vehicle compartment of a vehicle where a driver's head is located, to obtain imaging data;
- determining positions of the driver's head and eyes based on the imaging data;
- determining, based on the determined position of the driver's head and eyes, whether the driver is in an alert state or a non-alert state, wherein the driver is determined to be in the non-alert state when the determined position of the driver's head is determined not to be within a predetermined driver head area region within the vehicle compartment or when the driver's eyes are determined to be angled to an extent so as to not be viewing an area in front of the vehicle; and
- outputting a warning to the driver when the driver is determined to be in the non-alert state.

23. The non-transitory computer readable medium according to claim 22, further causing the computer to perform the function of:
- temporarily disabling outputting of a warning when a driver alertness signal is received.

24. The non-transitory computer readable medium according to claim 22, further causing the computer to perform the function of:
- detecting rotation of a steering wheel of the vehicle,
- wherein the driver alertness signal is output upon rotation of the steering wheel of the vehicle by at least a predetermined amount.

25. The non-transitory computer readable medium according to claim 24, wherein the predetermined rotation amount corresponds to +/−15 degrees from a center position of the steering wheel.

* * * * *